United States Patent [19]

Hale et al.

[11] Patent Number: 5,252,740
[45] Date of Patent: Oct. 12, 1993

[54] FLUORESCENT POLY(ARYLPYRIDINE) RARE EARTH CHELATES

[75] Inventors: Ron L. Hale, Woodside; Dennis W. Solas, San Francisco, both of Calif.

[73] Assignee: Baxter Diagnostics Inc., Deerfield, Ill.

[21] Appl. No.: 769,971

[22] Filed: Oct. 2, 1991

Related U.S. Application Data

[60] Continuation of Ser. No. 339,287, May 19, 1989, Pat. No. 5,116,989, which is a division of Ser. No. 118,292, Nov. 6, 1987, Pat. No. 5,032,677.

[51] Int. Cl.$^5$ .................. C07D 213/79; C07D 213/02
[52] U.S. Cl. .................. 546/263; 546/256; 544/209; 436/800
[58] Field of Search ............... 546/256, 263; 544/209; 436/800

[56] References Cited

U.S. PATENT DOCUMENTS

| | | |
|---|---|---|
| 4,379,931 | 4/1983 | Plueddemann ............ 546/14 |
| 4,801,722 | 1/1989 | Hinshaw et al. ........... 546/88 |
| 4,859,777 | 8/1989 | Toner ...................... 546/256 |

Primary Examiner—Murkund J. Shah
Assistant Examiner—Matthew V. Grumbling
Attorney, Agent, or Firm—Tilton, Fallon, Lungmus & Chestnut

[57] ABSTRACT

A class of fluorescent rare earth chelates and the ligands upon which they are based whose molecular structure incorporates a plurality of substituted arylpyridine di-acid units attached to a central template structure is disclosed. These ligands function as efficient energy transfer groups in fluorescent tagging reagents and tracers.

9 Claims, 11 Drawing Sheets

SCHEME I

SCHEME II

SCHEME III

SCHEME IV

SCHEME V

SCHEME VI

SCHEME VIII

SCHEME IX

SCHEME X

SCHEME XII

SCHEME XIII

FLUORESCENT POLY(ARYLPYRIDINE) RARE EARTH CHELATES

This is a continuation of application Ser. No. 07/339,287, filed May 30, 1989; now U.S. Pat. 5,116,989, which is a division of application Ser. No. 118,292 filed Nov. 6, 1987, now U.S. Pat. No. 5,032,677.

BACKGROUND OF THE INVENTION

1. Field of the Invention

This invention concerns compounds having a plurality of aryl substituted pyridine groups and their use as components of fluorescent chelate labels for fluoroassay techniques.

2. Background Art

Fluoroassay techniques are finding increasing application in chemical, biochemical and medical analyses. Fluorescence measurement methods are intrinsically extremely sensitive. However, the sensitivity of fluorescence assays, in practice, is limited by the presence of background fluorescence.

U.S. Pat. Nos. 4,150,295 and 4,058,732; issued on Apr. 17, 1979 and Nov. 15, 1977, respectively, and a chapter appearing at pages 67–80 of *Immunofluorescence and Related Staining Techniques*, Knapp, et al eds. (1978, Elsevier/North Holland Biomedical Press) disclose the general concept that background fluorescence has a relatively short life and that one can advantageously employ as measured fluorescent species, materials having a longer lived fluorescence. This work further points out that by using an intermittent excitation source and a time-coupled measurement of fluorescence one could essentially avoid or reject the background fluorescence while measuring the desired fluorescence.

Rare earth chelates have been identified by the art as materials having long-lived fluorescence. Such materials include a rare earth metal ion such as terbium or europium chelated by one or more ligands such as amine polyacids (See, U.S. Pat. No. 4,352,751 of Wieder and Wollenberg), "heteroatom-containing groups" including iminodiacetate substituted phenols, coumarins and phenanthrolines (See, Eastman Kodak European Patent Application 0068875) and aromatic diketones (See, German OLS 2,628,158), to point out a number of representative disclosures.

The present invention concerns a family of aryl pyridine derivatives which may be incorporated into long-lived fluorescent species with rare earth metals. The individual aryl pyridine units which are incorporated in the present compounds are disclosed in our copending U.S. patent application Ser. No. 712,744 filed Mar. 18, 1985, now U.S. Pat. No. 4,761,481. References to the general class of substituted pyridine derivatives include U.S. Pat. No. 4,008,239, 3,970,662 and 3,907,808 as well as Carbeteas and Williams, *J. Heterocycl. Chem.*, 11(5), 819 (1974); Weller and Luellen, *Tetrahedron Letters*, Vol. 22, No. 44, pp 4381-84 (1981) and Weller, Luellen and Weller *J. Org. Chem.*, 47, 4803-06 (1982). The above-noted European Patent Application 0068875 is also of interest Another reference of interest is WO/84/04970 which discloses a polymer with multiple units of visualization monomer.

STATEMENT OF THE INVENTION

We have now discovered a class of fluorescent rare earth chelates and the ligands upon which they are based whose molecular structure incorporates a plurality of substituted arylpyridine diacid units attached to a central template structure. These ligands function as efficient energy transfer groups in fluorescent tagging reagents and tracers. As compared to substituted phenylpyridine rare earth chelates containing a single phenylpyridine tetraacid group, these materials exhibit greater extinction coefficients and longer excitation wavelengths which lead to improvements in the sensitivity of detection of the fluorescent label.

The present fluorescent chelates contain a plurality of aryl-substituted pyridines arranged structurally within a single molecule such that each optimally binds to a single metal ion. Each pyridine group is structurally insulated from the others so that, in the unchelated form, each retains to some degree the properties of the single pyridine. At the same time, however, changes and improvements are observed in the properties of the chelates. For example, a diacid having a given substitution pattern and a certain sensitivity of detection for terbium and europium will generally become a better fluorophore for europium when incorporated as a part of a polymer compound. Improvements include increased molar absorptivity and longer excitation wavelengths. To the extent that these changes result in increased fluorescence emission, the result is increased sensitivity of detection of analytes tagged with these labels.

The ligands of this invention can be represented as a multi-site attachment molecule or "template molecule" (TM) to which are covalently attached a plurality (2 to 6 inclusive) of aryl-substituted pyridine diacids of the structure shown in General Formula I. This covalent coupling results in the ligand shown generally in General Formula II. This ligand can, in turn, give rise to the chelate shown generally in General Formula III.

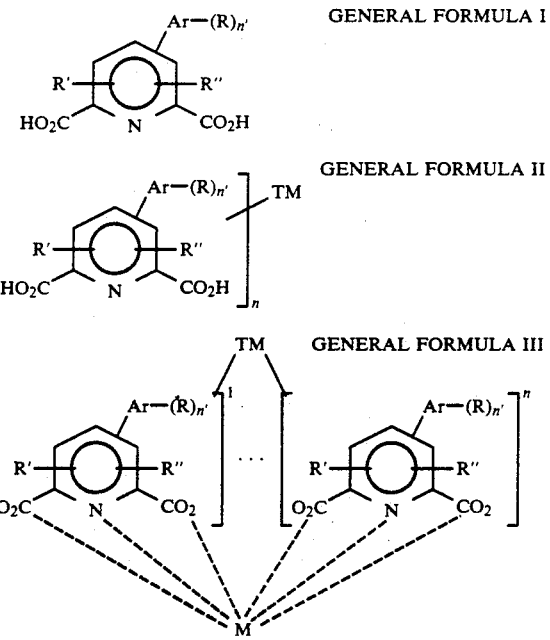

In these formulas, Ar is an aryl; TM is the multi-site attachment or template molecule; n is an integer from 2 to 6 inclusive, preferably 3 to 5 inclusive and more preferably 3 or 4; n' is an integer equal to the number of available bonding sites on Ar; M is a rare earth metal, generally in the form of its ion; and R, R' and R" are independently selected from hydrogen and electron-releasing groups including lower alkoxy, lower alkyl amino, di lower alkyl amino, aryl and aryloxy. This definition of these various R groups is subject to the proviso that preferably at least one of the R substituents on the Ar group is electron-releasing. The point of attachment of the TM molecule to the arylpyridine group can be directly to the Ar or to one of the n' R groups. In a variation, one of the two carboxylic acid groups on the pyridine can provide the attachment point.

In another aspect, this invention provides fluorescently detectable tagged molecules and especially fluorescently tagged bioactive molecules. These molecules are fluorescently detectable because they covalently incorporate a poly(arylpyridine) chelate of General Formula III. This covalent incorporation can be carried out in several manners. In one case the covalent bond is effected through a bondable site on one of the various Rs, R's and R"s. In an alternative, the bondable site is located directly on the template molecule such that the link is provided directly from the template molecule.

The covalent bonding can take the form of a simple single covalent bond such as a carbon-carbon bond, a carbon-nitrogen amine, amide or sulfonamide bond or the like between the chelate tag and the molecule to be tagged. It can also take the form of a specifically-added spacer- or linking moiety which contains the desired bonding site. These spacer moieties will at times be separately described to set forth in more detail their structures and properties. However, for simplicity, when presenting structural formulae such as Formula III they will not be separately shown and are to be considered part of the various Rs and/or Ar groups.

The molecules labelled with the poly(arylpyridine) groups of this invention may include a biologically active material, that is, one half of a biospecific (e.g., immunologic) pair so as to permit biospecific assays to be conducted by observing the fate, position or amount of the fluorescence imparted to the biospecific reaction by the present chelates.

DETAILED DESCRIPTION OF THE INVENTION

Brief Description of the Drawings

This invention will be further described with reference being made to the accompanying drawings which depict thirteen chemical reaction sequences denominated Scheme I through Scheme XIII respectively. These reaction schemes are useful for preparing materials of the invention.

DESCRIPTION OF PREFERRED EMBODIMENTS

Figure 1:
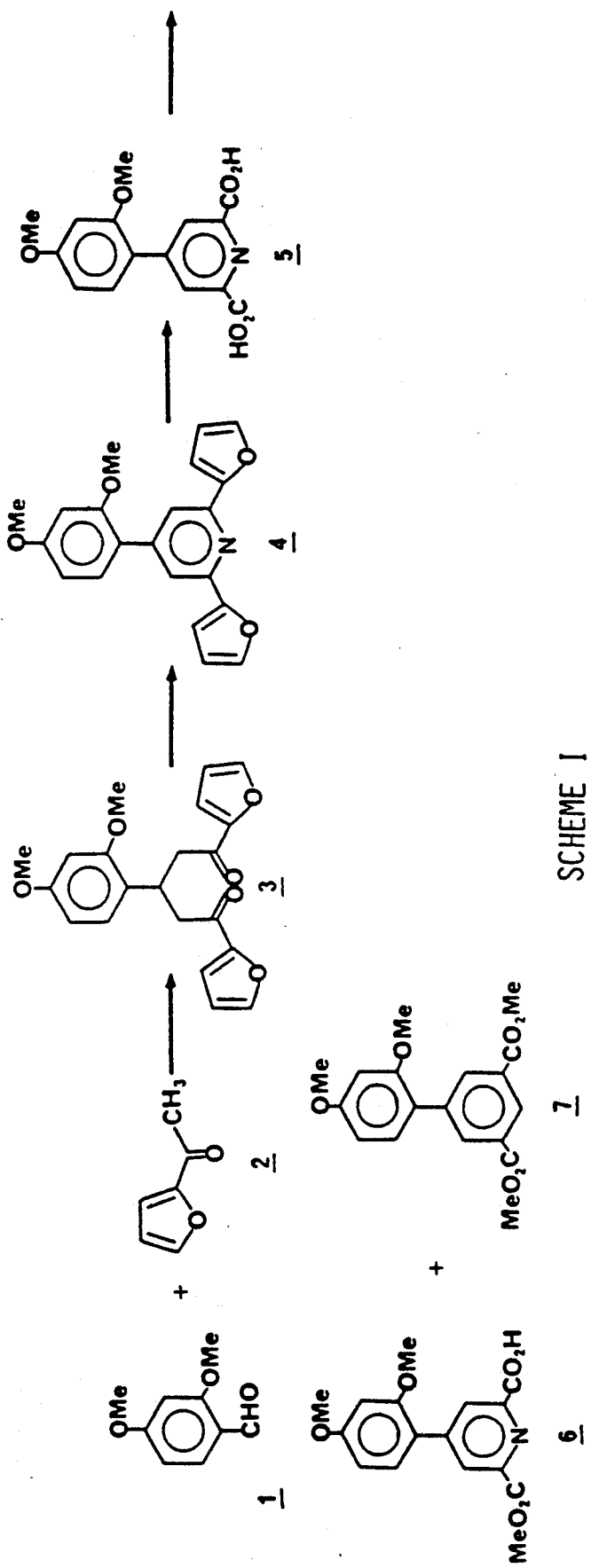
Figure 2:
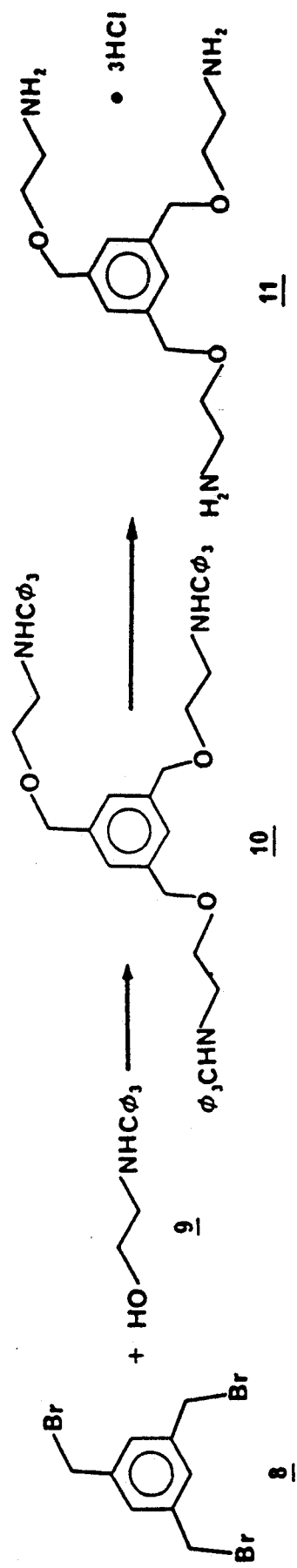
Figure 3:
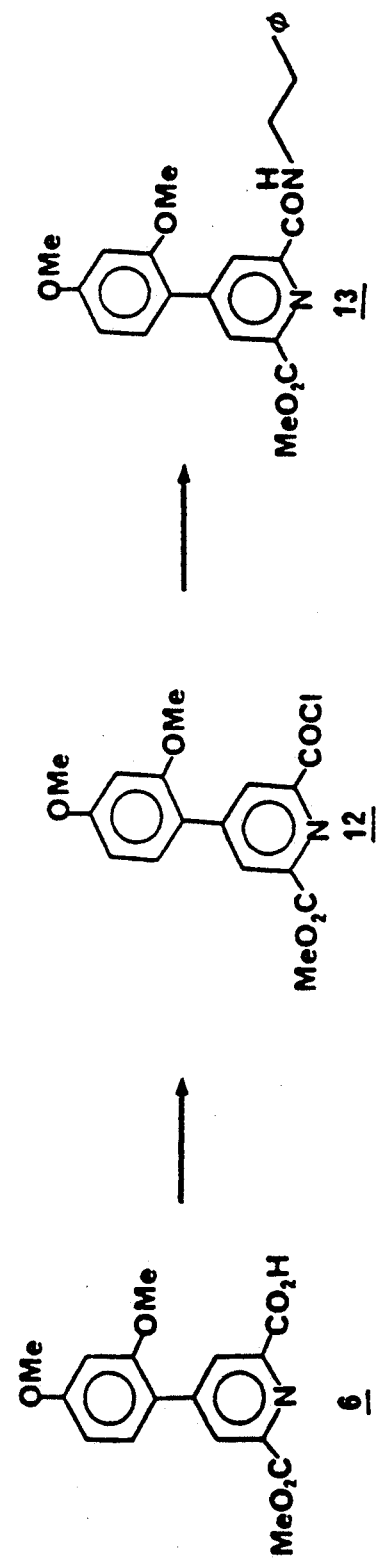
Figure 4:
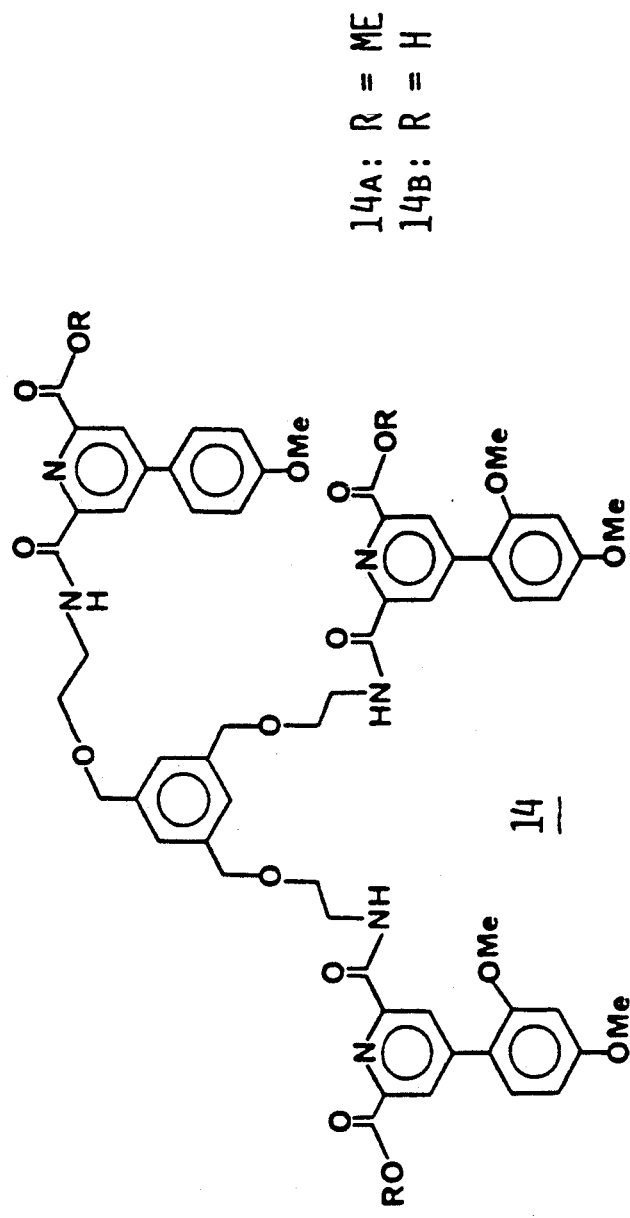
Figure 5:
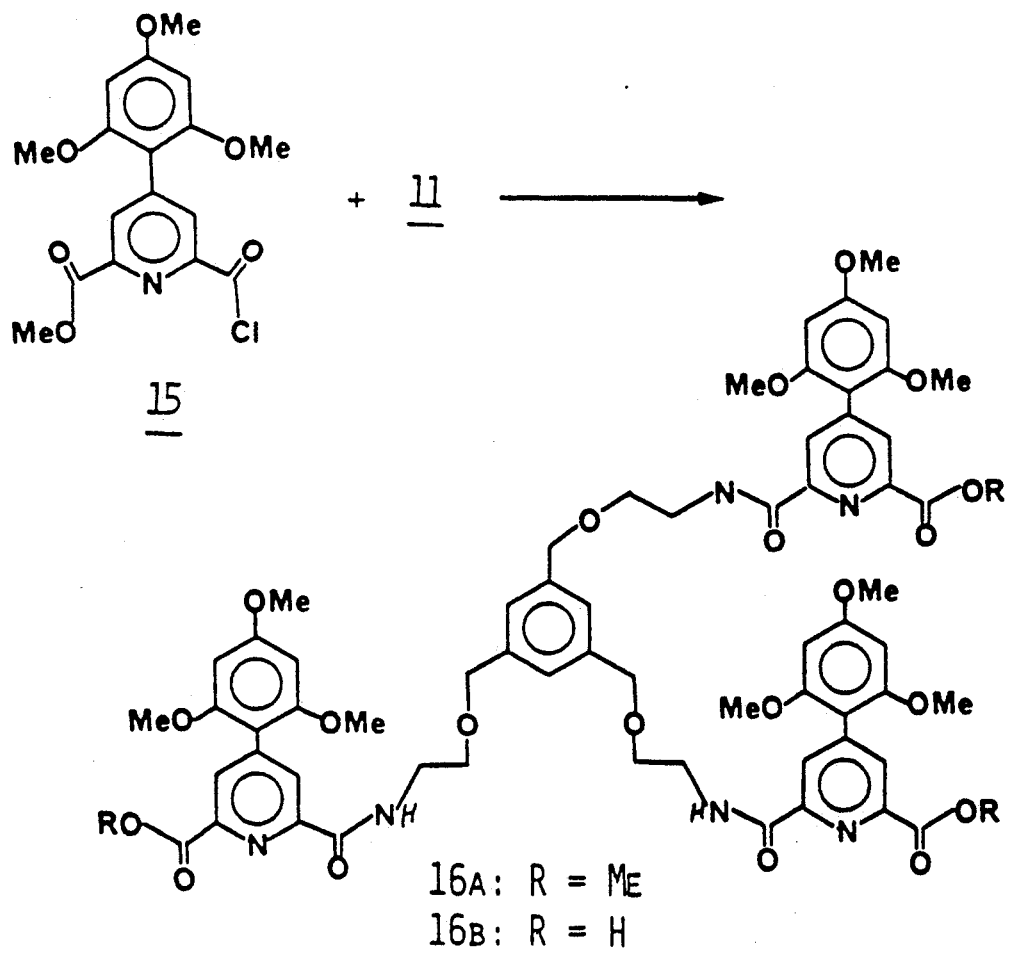
Figure 6:
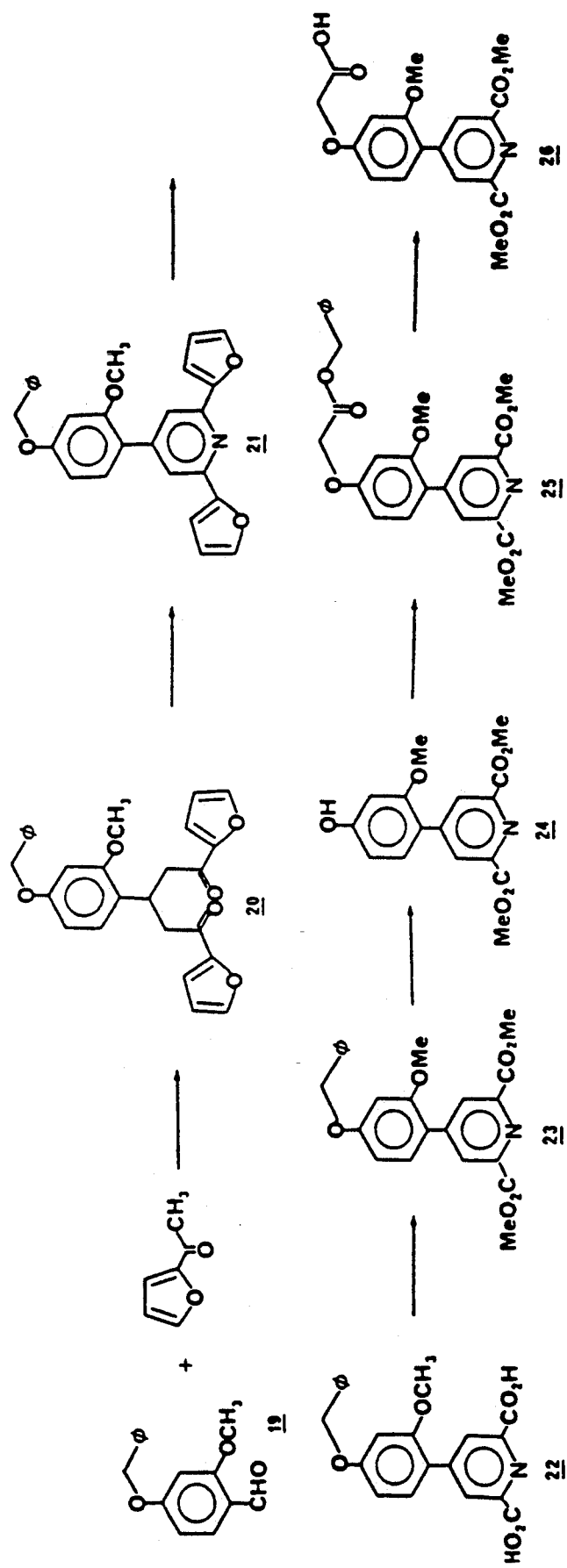
Figure 7:
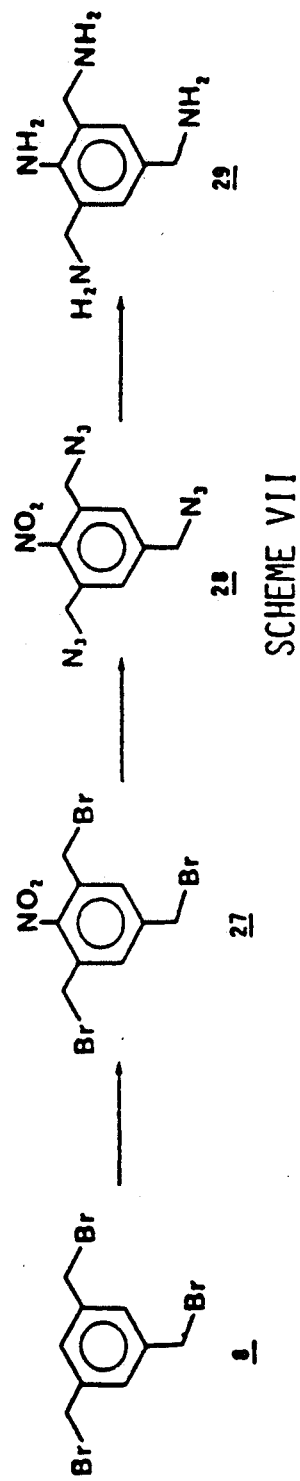
Figure 8:
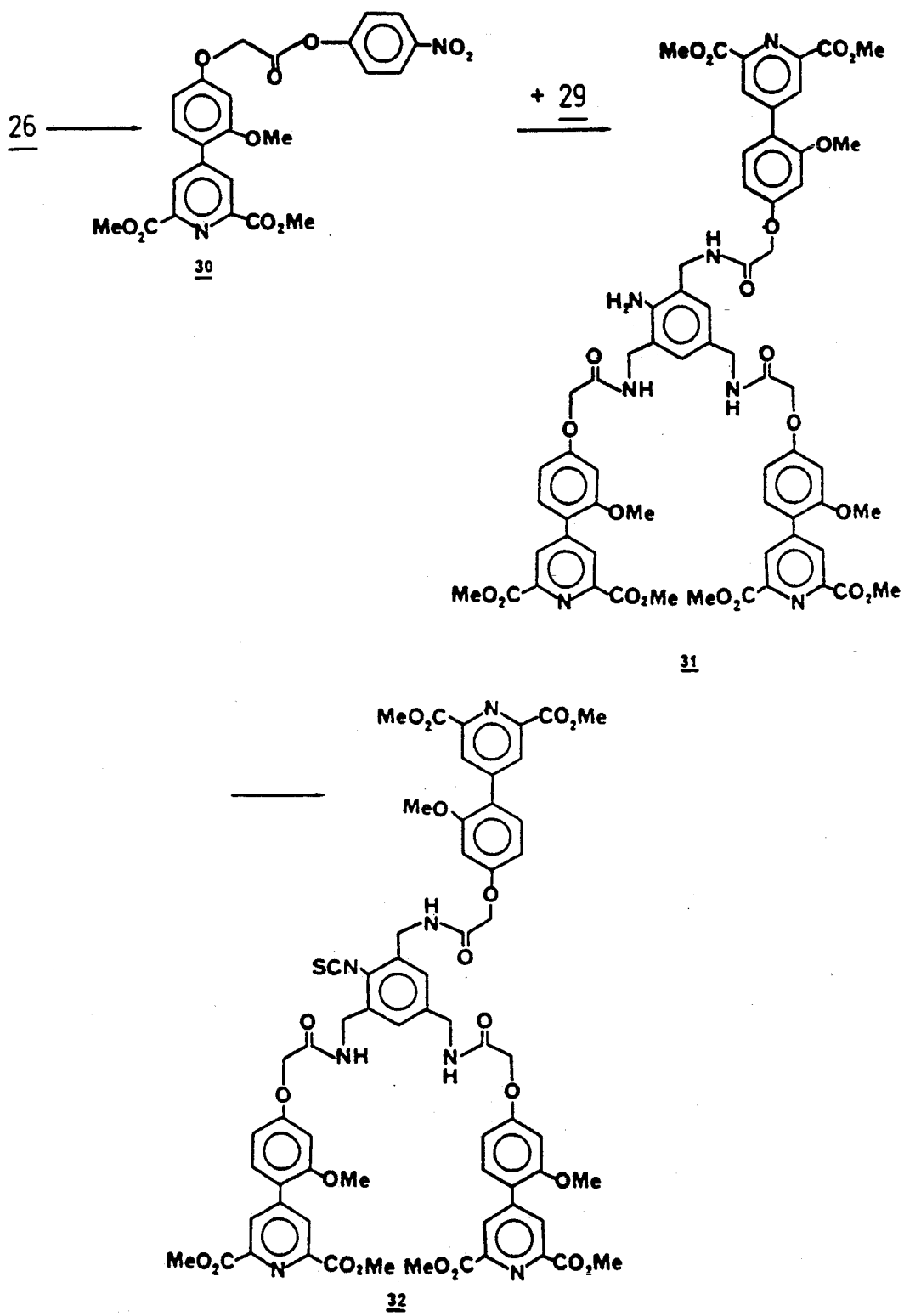
Figure 9:
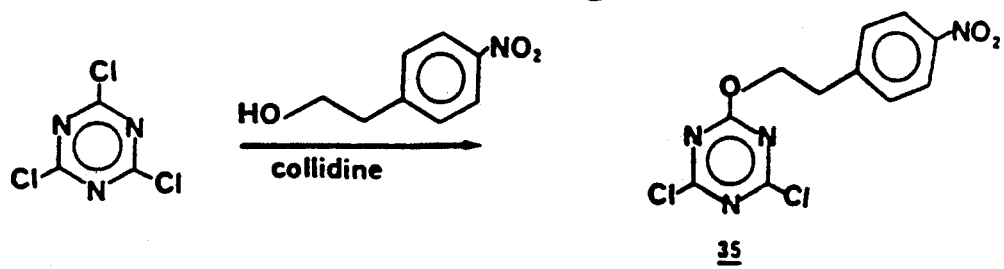
Figure 10:
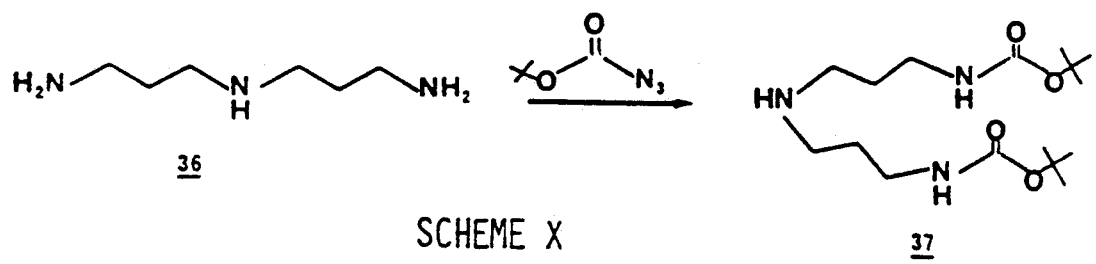
Figure 11:
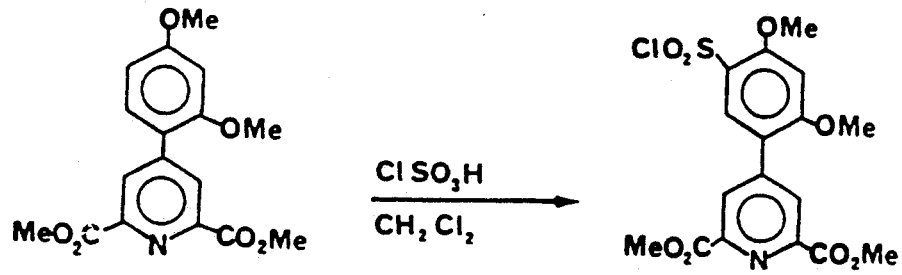
Figure 12:
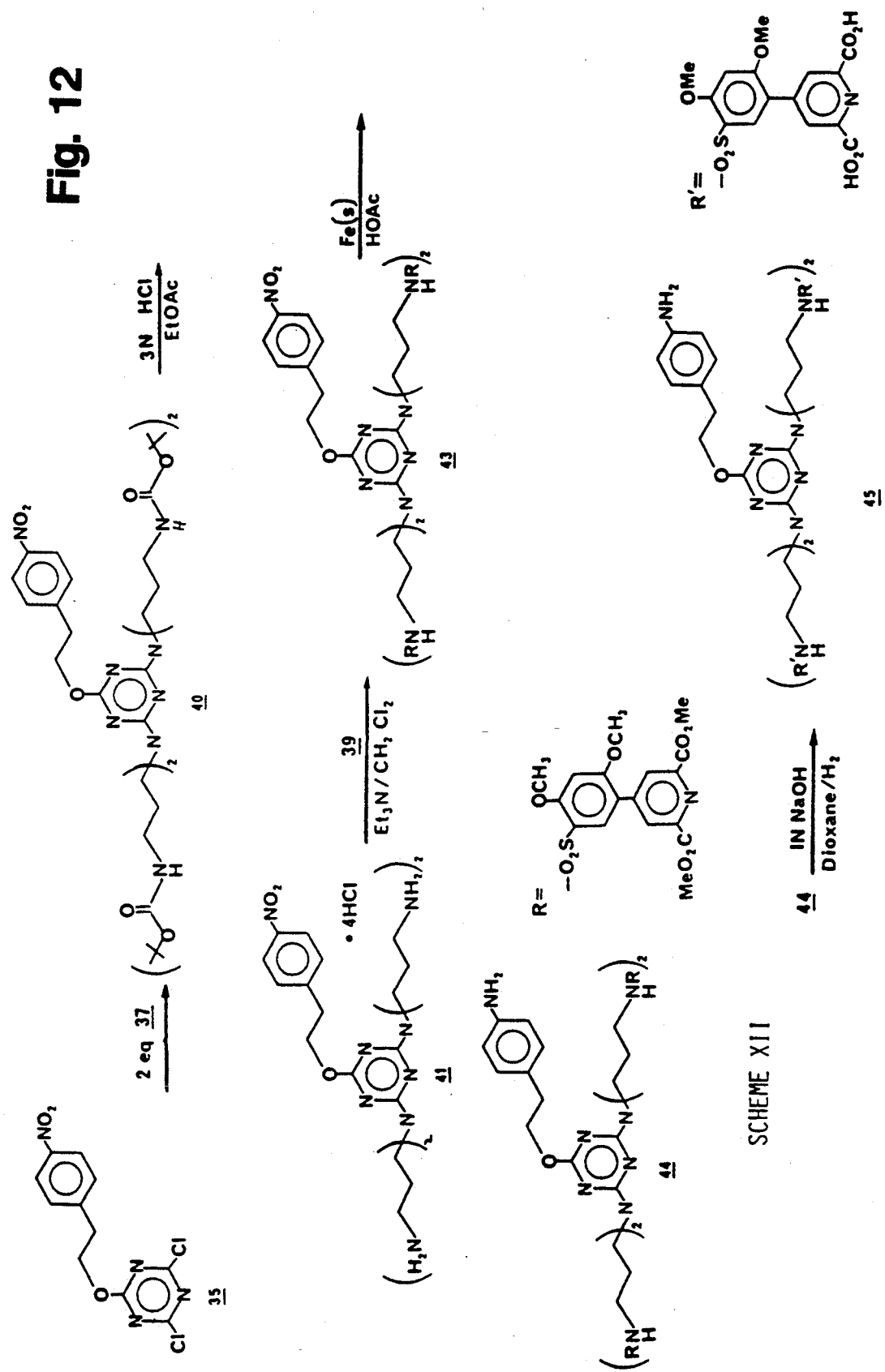
Figure 13:
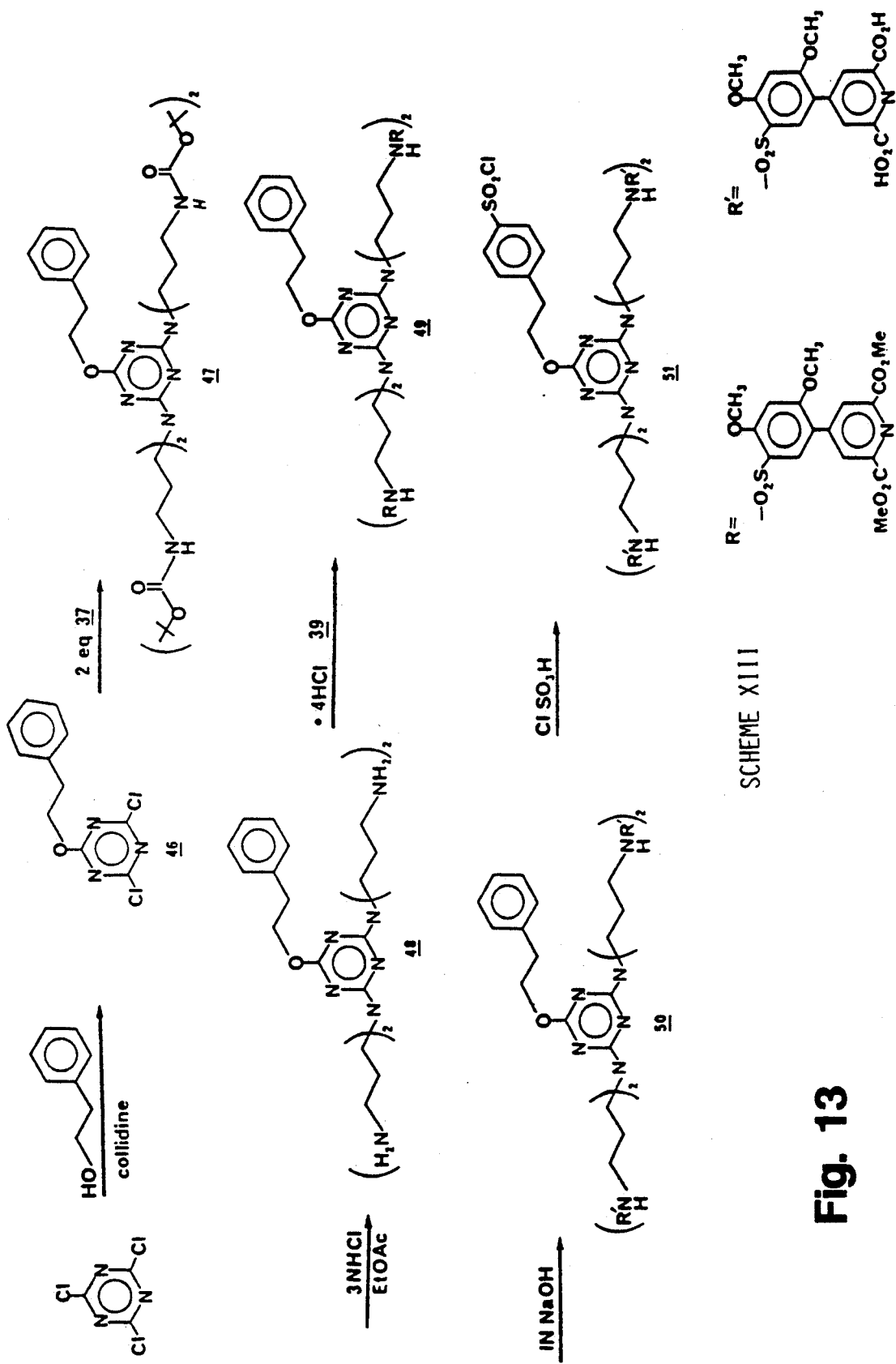

This Description of Preferred Embodiments is arranged in the following sections:
1. The Multi-site Attachment Groups
2. The Arylpyridine Dicarboxylic Acids
3. Linking Groups
4. The Biospecific Group
5. The Target Molecule
6. The Rare Earth Metal
7. Preparative Methods
8. Examples

1. The Multi-Site Attachment Groups

The ligands of the invention include a multi-site attachment or "template" group (TM) which provides 2, 3, 4, 5 or 6 covalent attachment sites for attaching the plurality of arylpyridine diacid units. These sites can be arranged symmetrically about or along the template or can be arranged asymmetrically.

The template is a covalently bonded organic molecule. It can be aliphatic or aromatic. Most commonly it provides at least 3 and up to about 20 atom chains between adjacent arylpyridine units. The template can present its n sites directly off of a core group such as the 1, 3, and 5 positions on a central phenyl ring or it can present its n sites as several groups of sites on several subcore units—for example two sites on each of two chains pendant from a aromatic central core.

The template molecules can be hydrocarbon or they can contain heteroatoms such as sulfur, oxygen and/or nitrogen. In preferred embodiments, the template molecule provides n aliphatic amines as attachment sites. The template molecule also may provide at least one additional bondable site to permit coupling of the polymeric ligand to active species, biologic materials and/or targets. The template may also carry additional groups to alter the chemical or physical properties (for example, solubility, ionic character or the like) of the ligand or the chelates it produces.

Representative templates include aliphatic materials such as 1,5,9-triaminononane with the three amine groups serving as attachment sites; tri(3-aminopropyl)methylene again with amine attachment sites; 1,3,5,7-tetra(2-aminoethyl)cyclooctane; and alkylene diamine-type materials such as

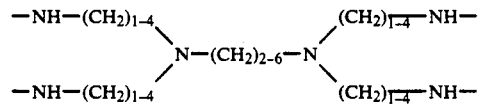

Aromatic based templates generally contain a benzene or naphthalene unit, a triazine unit or the like. With these groups the attachment points can be on the aromatic ring(s) or on groups attached to the aromatic ring(s). Typical materials include simple aromatics such as

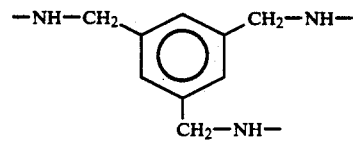

,

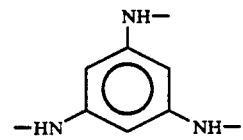

,

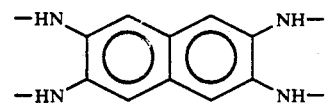

and

-continued

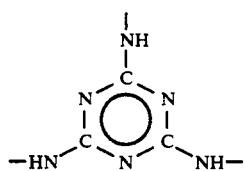

as well as more complex materials such as

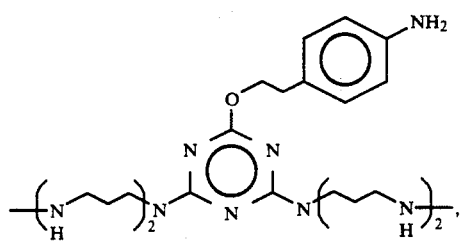

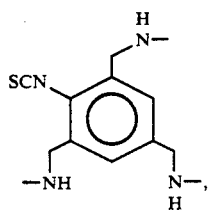

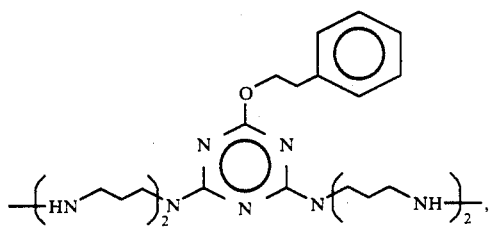

and

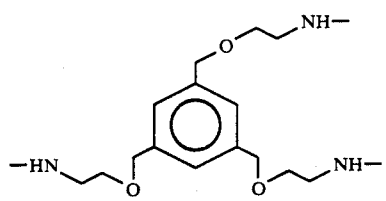

2. The Arylpyridine Dicarboxylic Acids

The ligands include a plurality (e.g. 2 to 6) of arylpyridine dicarboxylic acid units. In these units, the aryl substituents are themselves substituted with at least one electron-releasing group. These diacid units are depicted in General Formula I. As shown in Formula I, the pyridine carries substituents R', R" and —Ar—(R)$_{n'}$. The R' and R" substituents may be hydrogens; electron-releasing groups such as lower alkoxies, that is 1 to 4 carbon alkoxies, especially methoxy or ethoxy; lower alkyls, that is 1 to 4 carbon alkyls such as methyls, ethyls, n and iso propyls and the like; aminos; alkyl, i.e., mono and di, and especially dialkylamino, for example, dialkylaminos wherein each of the alkyls is from 1 to 4 carbons such as dimethylamino; aryls of six carbons and arylalkyls of up to about 9 carbons such as phenyls or benzyls and the like, subject to the limitation that such aryls are pendant from and not fused to the pyridine ring and aryloxies or arylalkyloxies of up to about 9 carbons such as phenyloxy or benzyloxy structures; and a linking group including a covalent bond and a bridge group providing a link to the template (TM) portion of the molecule as will be described. They can also include a linking group capable of joining the polymeric ligand as a whole to the target or other species being tagged.

The Ar—(R)$_{n'}$ substituent on the pyridine ring is an aryl, itself containing n' R substituents. The aryl is either a phenyl or a naphthyl ring. The number n' is an integer corresponding to the number of covalent bonding sites available on the Ar substituent, i.e., 5 in the case of a phenyl or 7 in the case of a naphthyl. The R substituents on the Ar group can be selected from the same groups as the R' and R" substituents.

Thus, the Ar—R$_{n'}$ substituents can be represented structurally by the General Formulae Ia and Ib.

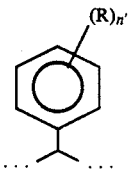    Ia

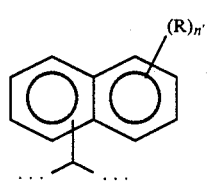    Ib wherein

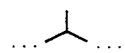

is a covalent bond to the pyridine ring depending upon whether the Ar unit is a phenyl or naphthyl. Phenyl is the preferred Ar unit.

While we believe that any of the aforesaid materials will work in accord with the present invention, our greatest experience is with materials having the Ar—(R)$_{n'}$ attached to the pyridine in the 4-position, i.e., para to the pyridine nitrogen, and on that basis this relationship is preferred. Also preferred are materials wherein the linking group to TM is one of the Rs as opposed to R' or R" and wherein one or both of R' and R" are hydrogens and especially wherein from one to three of the Rs are lower alkoxies and the rest of the Rs are hydrogen.

3. Linking Groups

The n pyridine diacids are coupled to the template molecule to give the desired poly(arylpyridine) ligand. The ligand itself in turn may be joined either directly from the template or through one of the pyridine diacid moieties to other groups such as a biospecific group, a target, or the like. Either of these couplings can be accomplished by a simple covalent bond or can be carried out through another linking functionality. This covalent bond or coupling functionality can constitute one of the positions denominated R', R" or R, and especially is one of the Rs. This coupling permits the fluorescent pyridine moieties to "tag" a biologically active biospecific group.

When the coupling is accomplished through a linking group this group should present an active or bondable site such as an amine, a hydroxyl, a carboxyl, an ester or the like to facilitate coupling of the biospecific group. Examples of such bondable R groups are the amino group (—NH$_2$) primary and secondary amine-terminated alkyls such as —CH$_2$—CH$_2$—NH$_2$ or

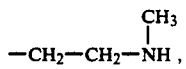

primary and secondary amine terminated aryls and aryloxies such as

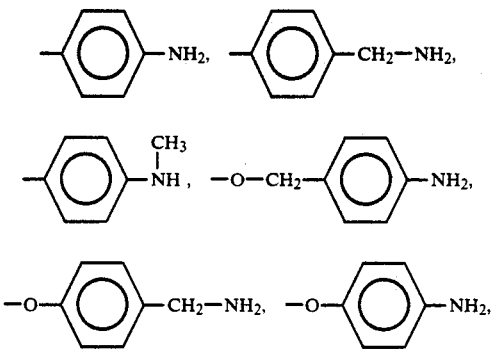

and the isomers thereof and the like; hydroxyl-containing alkyls such as —CH$_2$—CH$_2$—OH,

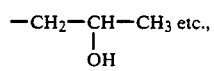

and hydroxyl-containing aryls and aryloxies such as

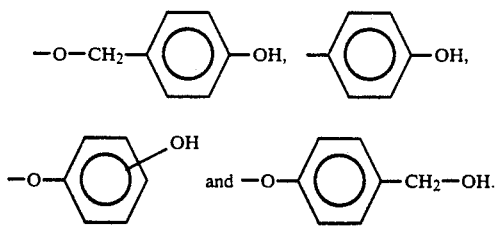

Other suitable functionalities for forming a bond to the biospecific group or to the template include amides, amidines, thioamides, ureas, thioureas, guanidines, diazos, thioethers, carboxy and phosphate esters, thiocyanates, thioesters and other covalent linkages such as are known in the art. As already noted a preferred linking group is the simple amino group. The linking groups can couple directly to the biologically active group or can be linked through a bifunctional spacer agent such as a member of the group —CO(CH$_2$)$_4$—, —CS—, —CO(CH$_2$)$_8$NHCOCH$_2$ON=, —COCH$_2$ON=, —CO(CH$_2$)$_5$NHCO(CH$_2$)$_6$CO—, —CO(CH$_2$)$_2$SS(CH$_2$)$_2$CO—, —CSNH(CH$_2$)$_3$N(CH$_2$CH$_2$)$_2$N(CH$_2$)$_3$NHCO(CH$_2$)$_6$CO—, —CSNH(CH$_2$)$_3$N(CH$_2$CH$_2$)$_2$N(CH$_2$)$_3$NHCO(-CHOH)$_2$CO—, —CSNH(CH$_2$)$_3$N(CH$_2$CH$_2$)$_3$NH-COCH$_2$ON= and the like. Such linking groups are representative and can alter and influence interactions between the fluorescent ligands and the biospecific groups.

4. The Biospecific Group

As noted above, in many advantageous applications a biologically active, i.e., biospecific group is linked to the ligand. The terms "biospecific group" and "biologically active group" are used in a broad sense to encompass all molecular structures which will "specifically recognize" or "specifically react" or "specifically interact" with another molecular species. Such groups can include immunologically specific groups such as antibodies and their respective antigens or haptens, hormones and their receptors, binding pairs such as the biotin/avidin pair and the like. They can also include nucleic acid sequences which will specifically hybridize with their complimentary sequences.

The biospecific groups can be selected to bind with or otherwise associate with a target molecule or can be selected to mimic or to include the target molecule so as to compete with the target in the biospecific reaction.

5. The Target Molecule

When a biospecific group is present in the chelate its target molecule or analyte may be a monoepitopic or polyepitopic material. It may be selected without limitation from materials such as drugs, metabolites, natural products, pesticides and contaminants of air and water. For purposes of illustration, one can list drugs including digoxin, digitoxin, phenytoin, theophylline, gentamicin, and tobramycin; alkaloids such as morphine, heroin, cocaine, ergot alkaloids, and the like; steroids such as the steroid hormones including estrogens and androgens, for example estradiol and anti-inflammatory steroids for example cortisol; lactams such as barbituates including phenobarbital; aminoalkylbenzenes such as the amphetamines; vitamins; prostaglandins such as F$_2$alpha and E; antibiotics and the like; and short peptide sequences or amino acids such as thyroxine, triiodothyronine and oxytocin. Representative pollutants and pesticides include PCB, dioxin, halogenated biphenyls, carbamates, thiophosphites, phosphate esters and their metabolites. Such materials can range in molecular weight from about 50 to about 1000.

The target molecule can also be a polymeric material such as a protein or other poly(amino acid), a polynucleic acid or a polysaccharide. Such protein materials can be taken from any of the classes of proteins including without limitation globulins, albumins, lipoproteins, glycoproteins, histones and the like, hypersensitive proteins including albumin, the immunoglobulins such as IgE, fibrinogen, transferrin, the various complement factors, the tumor markers like CEA (carcinoembrionic antigen) and PAP, the various blood clotting factors and protein hormones including beta-hCG, FSH, gastrin, LH and prolactin; insulin, thyrotropin, gonadotropin and the like. Examples of biospecific polysaccharides are those derived from microorganisms such as those associated with various species of Salmonella, Streptococcus, and Klebsiella. Other targets include materials responsive to infectious disease conditions such as infection with hepatitis or rubella.

The foregoing list is intended to be a brief outline. It is to be recognized that other equivalent materials such as are listed in more detail in the art (see, U.S. Pat. No. 4,193,983, columns 7–11 incorporated herein by reference) could be used in conjunction with the fluorophores provided by this invention.

In addition to the compounds just described wherein one of the R, R' or R" groups is a link to a biospecific biologically active group, this invention also provides other materials of the same general structure which do not contain a link to a biospecific material, that is where all of the R, R' and R"s are hydrogens or electron-releasing groups. Such materials are useful as chelating agents for metals and when chelated to rare earth metals give a fluorescent species which can serve as an indicator for quantitative or qualitative fluorescent measurement of rare earth metal ions in solutions.

In yet another variation, one of the carboxylic acid groups can provide the link to the bioactive molecule.

6. The Rare Earth Metal

The poly(arylpyridine diacid) ligands of this invention form long-lived fluorescent chelate complexes with rare earth metals including terbium, dysprosium, europium, samarium, and neodymium, in the form of their ions. Terbium and europium ($Tb^{+++}$ and $Eu^{+++}$) are preferred rare earth metal ions. These complexes are representatively shown in General Formula III.

1. Preparative Methods

The materials of this invention can be prepared as follows: First, two intermediates are prepared—one providing the n diacid units and the other the template molecule. Then these two materials are coupled.

This preparation technique will be illustrated by the following four representative preparations. In these preparations reference will be repeatedly made to the several schemes set forth in the figures and the compounds will be identified using the indicator numbers given in the figures. The same numbers are employed in the Examples.

In the first two preparations, two trimers 14 and 16 are formed. In these preparations half-acid chlorides 12 and 15 are representative diacid precursors and triamine 11 is a representative template molecule.

To produce the half-acid chloride 12, 2,4-dimethoxybenzaldehyde 1 and two equivalents of 2-acetylfuran are condensed with base to afford the dione 3. The dione is in turn reacted with hydroxylamine hydrochloride and the resulting difuryl pyridine 4 oxidized to the diacid 5 (Scheme I). The diacid is converted into the half acid-ester 6 to allow for the formation of the desired acid chloride 12 which will be used for coupling. This can be carried out by the slow addition of one equivalent of methanol to the diacid chloride of 5. This produces the mixture of the diester 7 and the half acid-ester 6. This mixture is easily separated by employing classical methods of separation such as by adding base to the reaction mixture and extracting followed by acidification of the aqueous layer regenerating the acid 6, and again extracting with organic solvent. There is minimal contamination by the diacid 5 in this workup.

Acid 6 is converted into the acid chloride by treatment with oxalyl chloride (Scheme III). The synthesis of the acid chloride analog 15 can be performed in the same manner starting with 2,4,6-trimethoxybenzaldehyde.

The second intermediate in the synthesis of the materials of this invention such as trimers 14 and 16 is the template molecule, such as triamine 11. A typical preparation starts with 1,3,5-trisbromomethyl benzene 8 and condenses it with N-tritylethanolamine 9 in the presence of sodium hydride to give protected triamine 10. Deprotection of the amine with refluxing hydrochloric acid in ethanol produced the triamine hydrochloride 11 (Scheme II).

To complete the synthesis of the trimer 14a, the acid chloride 12 is added to a solution of the triamine hydrochloride 11 with an excess of triethylamine (Scheme IV). The resulting compound is next saponified to form the triacid 14b. In an analogous manner the acid chloride 15 and the amine hydrochloride 11 afforded 16a and after saponification 16b (Scheme V). Both of the triacid trimers showed moderate to strong intensity emission spectra when converted into chelates with terbium and europium.

The synthesis of a third representative timer 32 involves, as in the first two cases, the formation of two intermediates, in this example, the acid 26 and the tetraamine 29 (Schemes VI and VII).

The initial steps in the synthesis of the acid 26 are exactly analogous to those used to produce the diacid 5 in Scheme I. The resulting diacid 22 is next esterified by sequential treatment with oxalyl chloride followed by methanol to afford the diester 23. Hydrogenation of the ester 23 followed by "O" alkylation of the phenol 24 with benzyl bromoacetate yields the triester 25. After hydrogenation of the benzyl ester the desired acid 26 is obtained.

The second intermediate 29 is also generated from the tribromide 8, as starting material, as was the triamine 11 in Scheme II. Nitration of 8 with nitronium tetrafluoroborate followed by treatment with sodium azide produces the triazide 27. Catalytic reduction of the nitro and azide group affords the tetraamine 29.

In order to couple the tetraamine 29 with the acid 26 the o-nitrophenyl ester of the acid is generated first. This is accomplished by treating 26 with p-nitrophenol in the presence of dicyclohexylcarbodiimide. The activiated ester 30 is then allowed to react with the tetraamine to produce the trimeric compound 31. To complete the synthesis of the isothiocyanate 32 the amine 31 was treated with thiophosgene in the presence of triethylamine (Scheme VIII). This material can be formed into chelates with Eu or Tb or the like.

EXAMPLES 1 AND 2

Preparation of Trimer Compounds 14 and 16 of Schemes I through V (A) 1,5-Di(2-furyl)-3-(2,4-dimethoxyphenyl)-1,5-pentanedione (3)

Following the general methos outlined by Weller and Luellen (see above), to a solution of 16.6 g (0.1 mole) of 2,4-dimethoxybenzaldehyde 1 and 20 ml (0.2 mole) of 2-acetylfuran 2 in 100 ml of methanol was added 5.5 g of potassium hydroxide previously dissolved in a small amount of methanol. The resulting mixture was heated to reflux and then stirred overnight at 55° C. The solution was then poured into water acidified with 1N HCl and extracted with $CH_2Cl_2$. The $CH_2Cl_2$ extracts were dried ($Na_2SO_4$) and the solvents removed at high vacuum. The resulting amber oil solidified on standing overnight affording 36.7 g of crude dione 3.

(B) 2-6-Di(2-furyl)-4-(2,4-dimethoxphenyl)pyridine (4)

To a solution of 38.7 g (0.1 mole) of "Crude" dione 3 in 352 ml of n-butanol was added 28 g (0.4 mole) hydroxylamine hydrochloride. The resulting mixture was heated to reflux and stirred for 3 hours. Upon cooling 500 ml of toluene and 500 ml of water were added and the aqueous phase made basic with 2N NaOH. The toluene layer was removed and aqueous phase was extracted twice more with toluene. The combined toluene extracts were dried ($Na_2SO_4$), the toluene was removed by rotary evaporation and the resulting oily residue was taken up into $CH_2Cl_2$. To $CH_2Cl_2$ solution was added 90 g of $SiO_2$ and the mixture swirled and allowed to stand for 15 minutes. The solution was then filtered and the solvent removed yielding a solid residue. Recrystallization from ethanol afforded 25 g (72%) of the pure pyridine compound 4.

(C) 4-(2,4-Dimethoxyphenyl)pyridine-2,6-dicarboxylic Acid (5)

To a solution of 1.05 g (3.02 mMole) of the pyridine compound 4 in 200 ml of t-butanol and 40 ml of water was added at 80° C., 6.19 g (0.0392 mole) of potassium permanganate in small portions. After addition is complete the mixture is stirred at 80° C. for 3 hours, filtered while still warm and the solvent is removed by rotary evaporation. The residue was taken up into 50 ml of water and acidified with 1N HCl to a pH of 2. The resulting yellow solid was filtered and dried in vacuo affording 702 mg (77%) of the diacid 5: IR (KBr) 3440 and 1720 (—$CO_2H$) and 1600 $cm^{-1}$ Rf=0.9 (reverse phase silica 70/30 : $MeOH/H_2O$).

(D) 4-(2,4-dimethoxyphenyl pyridine-2,6-dicarboxylic acid dimethyl ester (7) and 4-(2,4-dimethoxyphenyl)-2-carboxypyridine-6-methyl-carboxylate (6)

To a suspension of 0.98 g (3.234 mmole) of diacid 5 in 5 ml of $CH_2Cl_2$ plus 1 drop of DMF was added in a dropwise fashion at 0° C., 0.7 ml (8.085 mmole) of oxalyl chloride. After addition, the mixture was allowed to come to room temperature with vigorous evolution of HCl gas and stirred for 2 hours. The solvent and unreacted oxalyl chloride was removed by rotary evaporation leaving the canary yellow diacid chloride (1.152 g).

To a solution of the diacid chloride (1.152 g [3.398 mmole]) in 10 ml of $CH_2Cl_2$ with 4.1 ml (10.2 mmole) of triethylamine was added in a dropwise fashion, 0.14 ml (3.398 mmole) of methanol in 5 ml of ethyl ether. The resulting mixture was allowed to stir overnight at room temperature after which 1 ml of water was added and the mixture allowed to stir for 3 hours longer. The solution was poured into water and the aqueous phase was made acidic with 50% $H_2SO_4$. The organic layer was separated and the aqueous phase extracted again with $CH_2Cl_2$. The combined extracts were dried and the solvents removed affording 0.813 g of a mixture of 6 and 7.

The crude mixture of esters 6 and 7 (831 mg) was taken up into a small volume of ethyl acetate (20 ml) and washed with pH 12 aqueous NaOH solution (75 ml) and the aqueous layer separated. After acidification with 50% aqueous $H_2SO_4$ the aqueous solution was extracted twice with $CH_2Cl_2$ to remove the acid-ester 6. Both the ethyl acetate and the $CH_2Cl_2$ solutions were dried ($Na_2SO_4$) and the solvent removed yielding 265 mg of 6 and 330 mg of 7.

(E) 1,3,5-Tris-[2-N-tritylamino)ethoxymethyl]benzene (10)

To a suspension of 0.17 g (4.2 mmole) of 60% NaH in 30 ml of DMSO was added 1.3 g (4.2 mmole) of N-tritylethanolamine 9. The resulting solution was stirred at 50° C. until all hydrogen evolution had ceased and a homogeneous solution was obtained. To this mixture, at room temperature, was added 0.5 g (1.4 mMole) of 1,3,5-tris/(bromomethyl)benzene 8 in 5 ml of DMSO in a dropwise fashion. The mixture was again allowed to stir at 60° C. for 3 hours, cooled, added to water and extracted with $CH_2Cl_2$. The $CH_2Cl_2$ extracts were washed with water and saturated sodium chloride, dried ($Na_2SO_4$) and the solvents removed. The crude product was purified via chromatography with alumina and $EtOAc/CH_2Cl_2$:5/95 affording 0.75 g (40%) of pure 10.

(F) 1,3,5-Tris[2-(amino)ethoxymethyl] benzene hydrochloride (11)

A suspension of 2.5 g (2.44 mmole) of the tritylated amine 10 in 45 ml of ethanol was heated to reflux under argon. To this refluxing solution was added 3 ml of concentrated hydrochloric acid whereupon the remaining undissolved tritylated compound went into solution. After reluxing for 45 minutes to 1 hour the light yellow solution was cooled and the ethanol was removed by rotary evaporation. The residue was taken up into a small quantity of ethanol and dripped slowly into a large amount of ethyl ether. The hydrochloride 11 separated out immediately as a white semisolid. The milky solution was centrifuged and the supernate, containing exclusively the triphenylmethanol discarded. The residue was dried overnight in vacuo affording 1.05 g of the hydrochloride 11.

(G) 4-(2,4-dimethoxyphenyl)-2-chlorocarboxy-pyridine-6-methyl carboxylate (12)

This preparation was carried out in the same manner as that of the formation of the mono and dimethyl esters of 6 and 7, employing 178 mg (0.561 mmole) of the acid 6 and 0.05 ml (0.618 mmole) of oxalyl chloride. Yield was 179 mg of crude acid chloride 12.

(H) 4-(2,4-Dimethoxyphenyl)-2-phenethylamido-pyridine-6-methylcarboxylate (13)

To a solution of 12.1 mg (0.1 mmole) of phenethylamine in 2 ml of $CH_2Cl_2$ with 0.12 ml of triethylamine was added at room temperature 33.5 mg (0.1 mmole) of the above acid chloride 12 in 1 ml of $CH_2Cl_2$. The resulting mixture was stirred for 4 hours, poured into water and extracted with $CH_2Cl_2$. The $CH_2Cl_2$ extracts were washed with water, 1% aqueous citric acid, NaCl (sat) solution, dried ($Na_2SO_4$) and the solvents removed affording 36 mg (86%) of the amido ester 13. This reaction was a model reaction which verified general conditions for fluorophore attachment.

(I) 1,3,5-Tris{2-[4-(2,4-dimethoxyphenyl)-2-carboxamidopyridine-6-methylcarboxylate]ethoxymethyl} benzene (14a) (2,4-dimethoxy-DPA-"trimer")

To a solution of 113 mg (0.279 mmole) of the triamine hydrochloride 11 in 10 ml of DMF with 0.3 ml of triethylamine was added in a dropwise fashion, below room temperature, 280 mg (0.936 mmole of the acid chloride 12 in 10 ml of $CH_2Cl_2$ with rapid stirring. The resulting mixture was allowed to stir at room temperature for 12 hours, poured into water and extracted with $CH_2Cl_2$. The extracts were washed with 1% citric acid, water, dried ($Na_2SO_4$) and solvents removed affording 330 g of the crude trimer 14. Chromatography with 2% methanol/ethyl acetate on "flash" grade silica yielded 55 mg (17%) of pure trimer Rf=0.33 (with EtOAc on silica).

(J) 1,3,5-Tris{2-[4-(2,4,6-trimethoxyphenyl)-2-carboxamidopyridine-6-methylcarboxylate]ethoxy-methyl} benzene (16a) (2,4,6-trimethoxy DPA-"Trimer")

This preparation was carried out in the same manner as that of the synthesis of the dimethoxytrimer 14, employing 158 mg (0.39 mmole) of the triamine hydrochloride 11 and 427 mg (1.17 mmole) of the acid chloride 15, which was constructed in the same fashion as the dimethoxy analog 12 using the aldehyde, 2,4,6-trimethoxybenzaldehyde as the starting material. The yield was 87 mg (17%) of the desired trimer 16 after chromatography of the crude material on silica with 7% methanol/ethyl acetate.

EXAMPLE 3

Preparation of Trimer Compound 32 by the Method of Schemes VI through VIII (A) 4-(2-methoxy-4-benzyloxyphenyl)pyridine-2,6-dicarboxylic acid (22)

This preparation was carried out in the same manner as that of the synthesis of the diacid 5 using the starting aldehyde 19. Yield over all, from 19, was 23%.

(B) 4-(2-methoxy-4-benzyloxyphenyl)pyridine-2,6-dicarboxylic acid dimethyl ester (23)

To a suspension of 10 g (0.026 mole) of the diacid 22 in 100 ml of $CH_2Cl_2$ and 7 drops of DMF was added, at 0° C., in a dropwise fashion 12 ml (0.138 mole) of oxalyl chloride. After addition the mixture was allowed to come to room temperature with vigorous evolution of HCl gas and stirred for 2 hours. The resulting homogeneous solution was then cooled in an ice bath and 20 ml of methanol in 40 ml of $CH_2Cl_2$ was slowly added. The resulting mixture was stirred for 30 minutes at room temperature and poured into 300 ml of water. The organic phase was removed, washed with 10% $NaHCO_3$, water, dried ($Na_2SO_4$) and solvents removed. The crude diester (15 g) was purified via plug filtration with $SiO_2$/EtOAc/$CH_2Cl_2$ (20:80) yielding 7.0 g (65%) of the diester (23):NMR ($CDCl_3$) 3.85 (s,3,$OCH_3$), 4.05 (s,6,$CO_2Me$), 5.1 (s,2,$OCH_2O$), 6.7 and 7.4 (m,3,—$C_6H_3O_2R_2$) 7.35 (s,5,—$C_6H_5$), 8.5 (s,2,—$C_5H_2N'$).

C) 4-(2-methoxy-4-hydroxyphenyl)pyridine 2,6-dicarboxylic acid dimethyl ester (24)

To a solution of 7 g (0.174 mole) of the diester 23 in 200 ml of ethanol was added 1.0 g of 10% Pd/C. The container for the resulting suspension was evacuated and filled with $H_2$ (repeated three times) and kept under a positive atmosphere by means of a hydrogen-filled rubber bladder for 60 hours with very rapid stirring. The mixture was then filtered to remove catalyst and the solvent was removed from the filtrate by rotary evaporation. The resulting oil was dried in vacuo yielding after several hours (4.9 g) 89% of the desired phenol 24 as a solid.

(D) 4-(2-methoxy-4-oxobenzylacetate phenyl)pyridine-2,6-dicarboxylic acid dimethyl ester (25)

To a solution of 4.9 g (0.016 mole) of the phenol 24 in 300 ml of dry DMSO was added 0.65 g (0.016 mole) of 60% NaH. The resulting mixture was stirred one hour at room temperature until $H_2$ evolution had ceased and a clear homogeneous solution was obtained. To this solution was then slowly added 4 ml (0.025 mole) of benzyl bromoacetate after which the mixture was stirred for 48 hours. The reaction was poured into 150 ml of 0.3N citric acid (aq.) and extracted with $CH_2Cl_2$. The $CH_2Cl_2$ extracts were washed several times with $H_2O$, dried ($Na_2SO_4$) and the solvent removed by rotary evaporation to afford an amber oil. Recrystallization from $CH_2Cl_2$/EtOH gave 2.4 g (50%) of the desired ester 25. mp. 122°–124° C.;NMR ($CDCl_3$) 3.8 (s,3,$OCH_3$) 4.1 (s,6, $CO_2CH_3$), 4.7 (s,2, $CH_2O$) 6.7 and 7.3 (m,3,—$C_6H_3O_2R_2$) 7.4 (s,5,—$C_6H_5$) 8.4 (s,2,—$H_2N$):

(E) 4-(2-methoxy-4-oxoacetic acid phenyl)pyridine-2,6-dicarboxylic acid dimethyl ester (26)

To a solution of 1.36 g (3 mmole) of the vinyl ester 25 in 100 ml of ethanol was added 0.25 g of 10% Pd/C.

The resulting suspension was evacuated and filled with $H_2$ (repeated three times) and kept under a positive $H_2$ atmosphere by means of a hydrogen-filled rubber bladder for 2.5 hours with very rapid stirring. The mixture was then filtered and the filtrate rotary evaporated. This afforded 800 mg (73%) of the desired acid 26.

(F) 2,4,6-Tris(bromomethyl)nitrobenzene (27)

To a solution of 5 g (0.014 mole) of the tribromide 8 in 100 ml of $CH_3CN$ was added, at room temperature and under argon atmosphere, in a dropwise fashion 3.72 g (0.028 mole) of nitronium tetrafluoroborate in 200 ml of $CH_3CN$. The solution was then stirred for 20 minutes longer, poured into water and the mixture extracted with $CH_2Cl_2$. The $CH_2Cl_2$ extracts were washed with 10% $NaHCO_3$, dried ($Na_2SO_4$) and solvents removed to afford 4.86 g (86%) of the desired nitro compound 27: NMR ($CDCl_3$) 4.5 (s,6,—$CH_2Br$), 7.55 (s,—$C_6H_2$).

(G) 2,4,6-Tris(azomethyl)nitrobenzene (28)

To 75 ml of diethylene glycol was added 1.4 g (0.021 mole) of sodium azide. The mixture was heated and stirred to obtain a homogeneous solution and then cooled to room temperature. To this solution was then added 2.8 g (0.007 mole) of the nitro compound 27 and the resulting mixture was heated to 100° C. and held there for 3 hours and then cooled and poured into water. The aqueous solution was extracted with $CH_2Cl_2$ and the extracts were dried ($Na_2SO_4$) and the solvents removed affording 1.53 g (77%) of the triazide 28: NMR ($CDCl_3$) 4.55 (s,6,—$CH_2N_3$), 7.5 (s,2,—$C_6H_2$): IR (neat) 2100 (—$N_3$) and 1530, 1360 cm$^{-1}$ (—$N_2$).

(H) 2,4,6-Tris(aminomethyl)aniline (29)

To a solution of 1.55 g (0.0054 mole) of the triazide 28 in 50 ml of methanol was added 0.4 g of 10% Pd/C 10%. The reaction mixture was then evacuated and filled with $H_2$ (three times) and kept under a positive $H_2$ atmosphere by means of a hydrogen-filled rubber bladder, for 12 hours with very rapid stirring. The reaction was filtered and the filtrate concentrated giving 0.79 g (81%) of the desired triamine 29:NMR ($CD_3OD$) 3.5 and 3.6 (s,6,—$CH_2NH_2$), 6.8 (s,2,—$C_6H_2$); IR (neat) 3320 (—$NH_2$).

(I) 4-(2-Methoxy-4-oxo-p-nitrophenylacetate phenyl)-pyridine-2,6-dicarboxylic acid dimethyl ester (30)

To a homogeneous solution of 398 mg (1.06 mmole) of the acid 26 in 20 ml $CH_3CN$ was added 153 mg (1.1 mmole) of p-nitrophenol. The mixture was cooled to 0° C. and 227 mg (1.1 mmole) of dicyclohexylcarbodiimide was added and the reaction allowed to come to room temperature. After stirring for 3 hours the reaction was concentrated via rotary evaporation to 5 ml and 60 ml of ethyl acetate was added. The resulting precipitate (urea) was filtered off and then washed with more ethyl acetate. The filtrate was then washed with 10% $NaHCO_3$ (three times), dried ($Na_2SO_4$) and the solvents removed. The crude product was purified via column chromatography with silica and 30/70 (EtOAc/$CH_2Cl_2$) affording 410 mg (78%) of the nitrophenylester 30.

(J) 2,4,6-Tris([4-(4-(2,6-di(methoxycarbonyl)pyridyl))-3-methoxyphenyl]oxyacetamidomethyl)aniline (31)

To a solution of 50 mg (0.28 mmole) of the triamine 26 in 10 ml of methanol with 0.12 ml of triethylamine was added in a dropwise fashion 410 mg (0.83 mmole) of the nitrophenylester 30 in 10 ml of $CHCl_3$. After stirring for 3 hours at room temperature the mixture was poured into water and extracted with $CHCl_3$. The extracts were washed with three portions of 0.1N NaOH, dried (Na$_2$SO$_4$) and solvents removed. The crude product was purified via column chromatography with silica and 20% MeOH/EtOAc yielding 176 mg (56%) of the amino-trimer 31:NMR (CHCl$_3$) 3.9 (s,9,OCH$_3$), 4.1 (s,18, CO$_2$Me), 8.45 (s,6,—C$_6$H$_2$N).

(K) 2,4,6-Tris([4-(4-(2,6-di(methoxycarbonyl)pyridyl))-3-methoxyphenyl]oxyacetamidomethyl)methylaminophenylisothiocyanate(4-carboxymethoxy-2-methoxyl Phenyldipicolinic acid dimethyl ester (32)

To a solution of 176 mg (0.14 mmole) of the amino-trimer 31 in 3 ml of CH$_2$Cl$_2$ with 0.04 ml (0.028 m mole) of triethylamine was slowly added 10 ml (0.141 mmole) of thiophosgene in 1 ml of CH$_2$Cl$_2$. After stirring for 1 hour at room temperature the reaction was heated to 50° C. and stirred for an additional 0.5 hour. After cooling to room temperature the solution was poured into water and the organic layer separated. The organic layer was washed with water, dried (Na$_2$SO$_4$) and the solvents removed yielding 120 mg (66%) of the isothiocyanate 32: IR (KBr) 3400 (—NHCO—) 2100 (—NCS) 1720 (—CO$_2$Me) and 1660 cm$^{-1}$ (—NHCO—).

EXAMPLE 4

Preparation of Tetrameric Ligand 45 by the Methods of Schemes IX through XII 2-p-nitrophenethoxy-4,6-dichlorotrizaine (35)

To a solution of 4.4 g (0.024 mole) of cyanuric chloride in 30 ml of acetone at less than 10° C. was added 4.0 g (0.024 mole) of p-nitrophenethyl alcohol in 6 ml of acetone and 3.2 ml (0.024 mole) of collidine in 6 ml of acetone in a simultaneous dropwise fashion. During the addition the reaction temperature was kept at or below 10° C. After addition the mixture was stirred overnight at room temperature, filtered and the filtrate poured into water. The resulting solid was collected via filtration and dried in vacuo affording 5.0 g (66%) of the triazine 35.

(B) Preparation of 3,3'-Di-t-butylcarbamatodipropylamine (37)

To a solution of 5 g (0.04 mole) of 3,3'-iminobispropylamine 36 in 27 ml of DMSO at about 10° C. was added in a dropwise fashion 10.9 g (0.076 mole) of t-butylazidoformate in 14 ml of ether. The solution was then stirred for one hour longer at room temperature, poured into 50 ml of water and extracted with 2×75 ml of ether. The ether extracts were combined and washed with 25 ml of 0.1N HCl and then 25 ml of water. All the water washes including the original aqueous layer were combined and brought to a pH 12 with 6N NaOH. The aqueous solution was extracted with 4×100 ml of ether. The extracts were washed with saturated NaCl solution (2×50 ml), dried (Na$_2$SO$_4$) and the solvent removed yielding, after trituration with petroleum ether, 5.0 g (40%) of the diprotected amine 37.

(C) Preparation of 4-(5-Chlorosulfonyl-2,4-dimethoxyphenyl)-2,6-pyridine dicarboxylic acid dimethyl ester (39):

To 10 ml of chlorosulfonic acid at ice bath temperature was added 2 g (0.006 mole) of the diester 7 in a dropwise fashion. Upon completion the reaction mixture was allowed to come to room temperature and stirred there for one hour. The mixture was then cautiously poured into 100 g of ice giving a yellow solid. The solid was extracted into CH$_2$Cl$_2$ and the extract washed twice with water, dried (Na$_2$SO$_4$) and the solvents removed affording 2.25 g (87%) of the chlorosulfonyl compound 39.

(D) Amination of 2-p-Nitrophenethoxy-4,6-dichlorotriazine with 37:

To a vigorously stirred suspension of 0.476 g (0.0015 mole) of the triazine 35 in 15 ml of H$_2$O at 0°–10° C. was slowly added 1 g (0.003 mole) of the amine 37 in 10 ml of acetone. About half-way through the addition, the product started to separate out and the stirring was stopped. The remainder of the amine was added quickly as the flask was swirled by hand. Upon completion, the mixture was sonicated to loosen the stir bar and the solution/suspension was stirred rapidly. To this reaction was added 159 mg (0.0015 mole) of Na$_2$CO$_3$ and the mixture allowed to stir at room temperature for thirty minutes. Next the reaction was heated slowly to 80° C. with a reflux condensor and held there for 2 hours. After cooling, the mixture was poured into water and extracted with CH$_2$Cl$_2$. The extract was dried (Na$_2$SO$_4$) and the solvent removed yielding 1.3 g crude 40. After plug filtration [SiO$_2$/EtoAc/CH$_2$Cl$_2$ (20/80)] 1.0 g (79%) of pure 40 was obtained.

(E) Deprotection of the amine groups in 40:

To 1.0 g (0.0012 mole) of the t-BOC-aminotriazine 40 was added 10 ml of 3N HCl in ethyl acetate. After the compound completely dissolved, the mixture was stirred for one hour at room temperature, evaporated to an oil and then re-dissolved in methanol and rotary evaporated a second time to a pale yellow oil. The oil was once more taken up into methanol, evaporated to dryness and the solid residue remaining was triturated with ether. The white solid was then suspended in ether, centrifuged and the ether layer decanted from the solid white hydrochloride salt. The salt was dried in vacuo at 40° for one hour affording 0.744 g (96%) of 41.

(F) Amidation of 41 with 4-(5-Chlorosulfonyl-2,4-dimethoxyphenyl)-2,6-pyridine dicarboxylic acid dimethyl ester (39):

To a suspension of 0.5 g (0.0008 mole) of the amine-hydrochloride 8 in 20 ml of CH$_2$Cl$_2$ was added all at once 1.4 ml (0.01 mole) of Et$_3$N. The mixture was then cooled to 5°–10° C. and 1.4 g (0.0032 mole) of the sulfonyl chloride 39 in 20 ml of CH$_2$Cl$_2$ was slowly added in a dropwise fashion. The reaction was then allowed to stir at room temperature for 30 minutes after which a TLC was taken. Little of the sulfonyl chloride 9 had reacted by TLC so an additional 100 mg of the amine 8 was added and stirring continued overnight. The mixture was then poured into water and extracted with CH$_2$Cl$_2$. The extract was washed with water, dried (Na$_2$SO$_4$) and the solvent removed yielding crude 43. After column chromatography with SiO$_2$/5MeOH/CHCl$_3$, 1.55 g (93%) of the desired tetraamide 43 was obtained.

(G) Reduction of the Nitro Moiety in the Tetraamide 43:

To a solution of 460 mg (0.221 mmole) of the nitrotetraamide 43 in 26 ml of acetic acid was added 1 g of iron dust. The mixture was heated with swirling until the solution started to effervescence at which point the solution was cooled and another 1 g of iron dust was added. The mixture was heated again and the heat removed after the effervescence started. This procedure was repeated until a total of 5 g of iron dust had been added. After quickly cooling the solution to room temperature it was filtered through a celite plug and the red-orange solution was diluted with 200 ml of CHCl$_3$. The CHCl$_3$ solution was then washed twice with 300 ml of saturated sodium bicarbonate solution, dried (Na$_2$SO$_4$) and the solvent removed affording, after immediate plug filtration through silica with 5% MeOH/CHCl3, 243 mg (54%) of the desired anilino compound 44.

(H) Saponification of the Anilino Octaester 44:

To 460 mg (0.225 mmole) of the anilino ester 11 in 20 ml of water was added 2.7 ml of 1N NaOH and 10 ml of dioxane. The mixture was swirled and sonicated until the reaction solution was homogeneous. The yellow solution was then stirred at room temperature for 2 hours and then at 40°-50° C. for 2 hours. The mixture was then poured into water and acidified to pH 3 with 1N HCl. The resulting light yellow precipitate was then collected via centrifugation and the acidic aqueous layer decanted off. The solid was washed with water twice collecting each time by centrifugation. The precipitate was then dried in vacuo at 40° C. affording 380 mg (87%) of the desired anilino-acid 45.

EXAMPLE 5

Preparation of the Chlorosulfonated Tetramer Ligand 51 by the Methods of Scheme XIII (A) Preparation of 2-Phenethoxy-4,6-Dichlorotriazine 46:

In a manner exactly analogous to the preparation of compound 35, using 4.4 g (0.0024 mole) of cyanuric chloride (1), 2.9 g (0.0024 mole) of phenethyl alcohol and 3.2 ml of collidine, 3.37 g (52% yield) of the desired compound 46 was obtained after plug filtration of the crude product on silica gel using methylene chloride.

(B) Amination of 2-Phenethoxy-4,6-Dichlorotriazine 46 with 37:

In the same fashion as in the preparation of compound 40, 1.0 g (0.0037 mole) of the triazine 46, 2.45 g (0.0074 mole) of the amine 37 and 392 mg (0.0037 mole) of sodium carbonate afforded, after column chromatography with silica gel and 80/20 (methylene chloride/ethyl acetate), 1.15 g (36% yield) of the desired compound 47.

(C) Deprotection of the Amine Groups in 47:

Using the procedure outlined for the preparation of 41, 1.15 g (0.00134 mole) of the triazine 47 and 20 ml of 3N HCl/ethyl acetate produced, in a quantitative fashion, 0.81 g of the hydrochloride 48.

(D) Amidation of 48 with the Dimethyl Ester 39:

As in the method used to generate compound 43 460 mg (1.072 mmole) of the sulfonyl chloride 39, 162 mg (0.27 mmole) of the amine salt 48 and 0.5 ml (0.0036 mole) triethylamine afforded after recrystallization from dioxane, 470 mg (86% yield) of the amido-triazine 49.

(E) Saponification of the Octaester 49:

As was described for the preparation of the triazine acid 45, 470 mg (0.231 mmole) of the ester 49, 2.8 ml (2.772 mmole) of 1N NaOH and 10 ml each of water and dioxane yielded 337 mg (76%) of the triazine octaacid 50.

(F) Chlorosulfonation of the Triazine-Carboxylic Acid 50:

To 1 ml of chlorosulfonic acid at 0° C. was added, in small portions, 331 mg (0.172 mmole) of the triazine acid 50. After addition, the mixture was then cautiously added to 30-50 g of ice and the resulting product, a light yellow solid, was collected by filtration affording, after drying in vacuo at room temperature overnight, 305 mg (88%) of the chlorosulfonated tetramer 51.

The ligands so formed in these examples are then coupled to targets as described and comingled with an excess of rare earth metal. When the chelates which result are irradiated with a burst of laser light they fluoresce identifying their presence. The fluorescence can be quantitated to identify and locate the coupled targets.

While the invention has been described with reference to these several examples, it is to be understood that they are not to be construed as limitations on its scope which is instead defined by the following claims:

We claim:

1. A poly (arylpyridine) ligand comprising a plurality of substituted arylpyridine diacid units covalently attached to a central template structure having the structural formula:

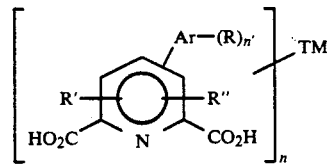

wherein Ar is an aryl; TM is the central template structure, said central template structure having a plurality of attachment sites for covalently attaching the plurality of substituted arylpyridine diacid units and wherein TM is selected from the group consisting of 1) a covalently bonded organic molecule containing hydrocarbons and optionally containing a heteroatom selected from the group consisting of oxygen, nitrogen and sulfur and having at least one aromatic unit and 2) a covalently bonded organic aliphatic molecule containing hydrocarbons and optionally containing a heteroatom selected from the group consisting of oxygen, nitrogen and sulfur; n is an integer from 2 to 6 inclusive, n' is an integer equal to the number of available covalent bonding sites in Ar; and R, R' and R" are independently selected from hydrogen and electron-releasing groups selected from the group of electron-releasing groups consisting of lower alkoxy, lower alkyl amino, di lower alkyl amino, aryl and aryloxy, and wherein TM provides at least three total and up to about twenty total atoms between adjacent substituted arylpyridine diacid units.

2. The ligand of claim 1 wherein n has a value from 3 to 4 inclusive.

3. The ligand of claim 1 wherein n has a value from 3 to 4 inclusive.

4. The ligand of claim 1 wherein at least one of the substituents on Ar is an electron-releasing group.

5. The ligand of claim 1 wherein at least one of the substituents on Ar is an alkoxy.

6. The ligand of claim 1 wherein at least one of the substituents on Ar is a methoxy.

7. The ligand of claim 1 wherein Ar—(R)$_n$, is a phenyl carrying n' R substituents.

8. The ligand of claim 7 wherein at least one of the substituents on Ar is an electron-releasing group.

9. The ligand of claim 8 wherein at least one of the substituents on Ar is an alkoxy.

* * * * *